United States Patent
Sofka et al.

(10) Patent No.: US 8,811,697 B2
(45) Date of Patent: Aug. 19, 2014

(54) DATA TRANSMISSION IN REMOTE COMPUTER ASSISTED DETECTION

(75) Inventors: Michal Sofka, Franklin Park, NJ (US);
Kristof Ralovich, Princeton, NJ (US);
Jingdan Zhang, Plainsboro, NJ (US);
Shaohua Kevin Zhou, Plainsboro, NJ (US); Gianluca Paladini, Skillman, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 411 days.

(21) Appl. No.: 13/080,891

(22) Filed: Apr. 6, 2011

(65) Prior Publication Data
US 2011/0243407 A1    Oct. 6, 2011

Related U.S. Application Data

(60) Provisional application No. 61/321,222, filed on Apr. 6, 2010.

(51) Int. Cl.
*G06K 9/00* (2006.01)
*G06K 9/62* (2006.01)
*G06T 7/00* (2006.01)

(52) U.S. Cl.
CPC ..... *G06K 9/6256* (2013.01); *G06T 2207/20016* (2013.01); *G06F 19/231* (2013.01); *G06T 2200/16* (2013.01); *G06T 7/0012* (2013.01)
USPC ........... 382/128; 382/131; 382/132; 382/154; 382/240

(58) Field of Classification Search
USPC ................ 382/128, 131, 132, 133, 154, 240
See application file for complete search history.

(56) References Cited

U.S. PATENT DOCUMENTS

| | | | |
|---|---|---|---|
| 6,314,452 B1 * | 11/2001 | Dekel et al. | 709/203 |
| 6,891,973 B1 * | 5/2005 | Atsumi et al. | 382/232 |
| 2005/0129271 A1 * | 6/2005 | Shi et al. | 382/100 |
| 2010/0119137 A1 | 5/2010 | Schwing et al. | |
| 2010/0240996 A1 | 9/2010 | Ionasec et al. | |

OTHER PUBLICATIONS

Tu Z. Probabilistic Boosting-Tree: Learning Discriminative Models for Classification, Recognition, and Clustering. In: CVPR. vol. 2; 2005. p. 1589-1596.
Viola P, Jones MJ. Rapid object detection using a boosted cascade of simple features. In: CVPR. vol. 1; 2001. p. 511-518.
Schnitzspan P, Fritz M, Roth S, Schiele B. Discriminative structure learning of hierarchical representations for object detection. In: CVPR; 2009. p. 2238-2245.
Zhang W, Zelinsky G, Samaras D. Real-time Accurate Object Detection using Multiple Resolutions. In: ICCV; 2007.

(Continued)

*Primary Examiner* — Tom Y Lu (57) ABSTRACT

For cloud-based computer assisted detection, hierarchal detection is used, allowing detection on data at progressively greater resolutions. Detected locations at coarser resolutions are used to limit the data transmitted at greater resolutions. Data is only transmitted for neighborhoods around the previously detected locations. Subsequent detection using higher resolution data refines the locations, but only for regions associated with previous detection. By limiting the number and/or size of regions provided at greater resolutions based on the previous detection, the progressive transmission avoids transmission of some data. Additionally, or alternatively, lossy compression may be used without or with minimal reduction in detection sensitivity.

20 Claims, 2 Drawing Sheets

(56) References Cited

OTHER PUBLICATIONS

Zhu L, Yuille AL. A Hierarchical Compositional System for Rapid Object Detection. In: NIPS; 2005. p. 1633-1640.

Sudderth EB, Torralba A, Freeman WT, Willsky AS. Describing Visual Scenes Using Transformed Objects and Parts. IJCV. 2008;77(1-3):291-330.

Vilaplana V, Marques F, Salembier P. Binary Partition Trees for Object Detection. TIP. 2008;17(11):2201-2216.

Butko NJ, Movellan JR. Optimal scanning for faster object detection. In: CVPR; 2009. p. 2751-2758.

Ringl H. Schernthaner R, Sala E. El-Rabadi K, Weber M, Schima W, et al. Lossy 3D JPEG2000 Compression of Abdominal CT Images in Patients with Acute Abdominal Complaints: Effect of Compression Ratio on Diagnostic Confidence and Accuracy. Radiology. 2008:248:476-484.

Dufaux F, Ebrahimi T. Scrambling for Video Surveillance with Privacy. In: CVPR Workshop; 2006.

Fleck S, Busch F, Biber P, Strasser W. 3D Surveillance A Distributed Network of Smart Cameras for Real-Time. In: CVPR Workshop; 2006.

Zheng, et al. in "Fast Automatic Heart Chamber Segmentation from 3D CT Data Using Marginal Space Learning and Steerable Features," Proc. Int'l Conf. on Computer Vision, pp. 1-8, 2007.

Agarwal A, Henehan N, Somashekarappa V, Pandya AS, Kalva H, Furht B. A Cloud Computing Based Patient Centric Medical Information System. In: Furht B, Escalante A, editors. Handbook of Cloud Computing. Springer US; 2010. p. 553-573.

Haux R. Health information systems—past, present, future. International Journal of Medical Informatics. 2006;75 (3-4):268-281.

Faggioni L, Neri E, Castellana C, Caramella D, Bartolozzi C. The future of PACS in healthcare enterprises. European Journal of Radiology. 2010; In Press, Corrected Proof.

Sofka M, Zhang J, Zhou SK, Comaniciu D. Multiple Object Detection by Sequential Monte Carlo and Hierarchical Detection Network. In: Proceedings of the IEEE Conference on Computer Vision and Pattern Recognition. San Francisco, CA; 2010.

Schelkens P, Skodras A, Ebrahimi T. The JPEG 2000 Suite. John Wiley and Sons; 2009.

\* cited by examiner

DATA TRANSMISSION IN REMOTE COMPUTER ASSISTED DETECTION

RELATED APPLICATIONS

The present patent document claims the benefit of the filing dates under 35 U.S.C. §119(e) of Provisional U.S. Patent Application Ser. No. 61/321,222, filed Apr. 6, 2010, which is hereby incorporated by reference.

BACKGROUND

The present embodiments relate to computer assisted detection (CAD). For computer assisted detection, previous discriminative approaches detect objects by testing entire images exhaustively at all locations. Thin-client devices (e.g., personal data assistants, cell phones, or tablet computers) may have the functionality to review medical data remotely, but do not have sufficient processing power and/or memory to rapidly detect from large data sets, such as medical scan data. Instead, CAD is performed on workstations for viewing at the workstation, but network bandwidth may limit performance.

Images may be visualized in a manner to minimize the amount of data to be transmitted. Data representation with a set of progressively increasing resolutions has been previously used to encode geometric meshes and for remote medical image visualization. The representation of images can be realized through the JPEG 2000 standard, which also includes client/server Interactive Protocol (JPIP) for transmitting image regions at desired resolutions using the least bandwidth required. The JPIP protocol is useful for visualizing large DICOM images remotely. The quality of JPEG 2000 images after lossy compression has been previously evaluated for reading radiology datasets.

Operating under bounded bandwidth resources has also been addressed in visual surveillance applications. Typically, these techniques process the two-dimensional images on the server where the cameras are attached. The extracted information, such as extracted regions and detected objects, has much smaller size than the original images and can be transmitted efficiently over a wide-area network. However, two-dimensional images require less bandwidth and less computational power. Detection in three-dimensional data sets may be more difficult and require greater transmission bandwidth.

BRIEF SUMMARY

By way of introduction, the preferred embodiments described below include methods, computer readable media and systems for data transmission in computer assisted detection. Hierarchal detection is used, allowing detection on data at progressively greater resolutions. Detected locations at coarser resolutions are used to limit the data transmitted at greater resolutions. Higher resolution data is transmitted for neighborhoods around the previously detected locations. Subsequent detection using higher resolution data refines the locations, but only for regions associated with previous detection. By limiting the number and/or size of regions provided at greater resolutions based on the previous detection, the progressive transmission avoids transmission of some data. Additionally or alternatively, lossy compression may be used without or with minimal reduction in detection sensitivity in CAD.

For operation with thin clients, a server obtains the data progressively and/or with lossy compression, and the server detects the locations. The detected locations are output to the thin client, allowing computer assisted detection without the processing and bandwidth limitations of the thin-client.

In a first aspect, a non-transitory computer readable storage medium has stored therein data representing instructions executable by a programmed processor for data transmission in computer assisted detection. The storage medium includes instructions for receiving, at a computer assisted detection processor and from the remote storage location, first data. The first data is down sampled data of data representing a region. The instructions are also for detecting, by the computer assisted detection processor and from the remote storage location, a plurality of first locations represented by the first data. The instructions provide for requesting and receiving, at the computer assisted detection processor, second data. The second data is additional data representing second neighborhoods around the first locations and not representing portions of the region outside of the second neighborhoods. The computer assisted detection processor detects a plurality of second locations represented by the second data. Positions are output to a client device different than the computer assisted detection processor and the remote storage location. The positions are a function of the second locations.

In a second aspect, a method is provided for computer assisted detection with data from a remote storage location. Image data representing a patient at progressively greater resolutions is received. A processor detects candidate locations hierarchally from the image data at the progressively greater resolutions. The image data for each of the resolutions is for the candidate locations detected from a lesser one of the resolutions. The received image data is free of data representing regions outside of neighborhoods around the candidate locations for any of the progressively greater resolutions.

In a third aspect, a system is provided for computer assisted detection with medical scan data from a remote storage location. A database is configured to store the medical scan data and configured to output the medical scan data in a lossy compression format. The medical scan data represents a region of a patient. A processor is configured to receive, through a network, the medical scan data from the database in the lossy compression format. The processor is configured to decompress the medical scan data and detect a location in the region from the decompressed medical scan data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Landmarks are automatically detected in three-dimensional (3D) volumes or two-dimensional (2D) planes in a cloud computing environment. A client, such as a thin client, communicates with a remote data analysis server for image analysis. The data analysis server implements a learning-based or other CAD algorithm. The data analysis server communicates with a remote data center or a local memory to acquire compressed image data. The algorithm uses compressed images in training and detection.

Performing CAD in the cloud computer environment allows integration, maintenance, and software updates to be implemented on the data analysis server rather than the client. When the models are updated, the updated models are immediately available to all clients. More complicated models may be built, such as models with several landmarks of interest trained for different modalities. Such large scale systems may require coordination of multiple CAD servers possibly distributed in a wide-area network.

Limited network or processing bandwidth relative to the amount of data is addressed by a hierarchical detection algorithm. Hierarchical detection allows detection using progressive transmission of only image regions required for processing. For example, the client sends a request for visualization of a specific landmark. The hierarchical detection algorithm running on the data analysis server starts detection on a coarse image obtained from data center, identifying coarse landmark location candidates. The neighborhoods surrounding the coarse landmark location candidates are then used to obtain image data at a finer resolution level, but for neighborhoods around the coarse landmark location candidates and not other regions. The hierarchical detection algorithm then detects landmark location candidates using the data at the finer resolution level, but only for the available neighborhoods. The refinement of the candidate locations continues at the subsequent, higher resolution levels. The final location or locations are computed as the robust mean of the strongest candidates or other detected locations at a highest or sufficient resolution. The feedback of candidates detected at a coarser resolution makes it possible to only transmit image regions at a finer resolution surrounding these candidates rather then the entire images. Higher, greater, finer, coarser, and lesser resolution are used interchangeably as relative terms to other resolution levels.

Hierarchical modeling typically focuses on exploiting multiple feature levels of different resolutions and on part-based or region-based architectures. These approaches may not use the locations detected at a different level for further detection. The hierarchical modeling for limiting bandwidth instead or additionally propagates the position candidate hypotheses during training and detection, exploring larger context at coarse resolutions and finishing with a highly accurate detection result at the finest resolution. The candidate propagation results in a more robust detector compared to algorithms that treat each resolution level independently.

An alternative bandwidth reduction for data transmission is provided. The image data, such as the higher resolution neighborhood data, are transmitted after performing lossy compression. For example, lossy compression is provided using the JPEG 2000 standard for three-dimensional data.

For computed tomography (CT) data, lossy compression used with progressive data transmission may provide approximately 30 times bandwidth reduction as compared to transmitting an entire volume data set for detection. For magnetic resonance imaging (MRI) data, the bandwidth reduction may be about a factor of 196. Similar accuracy when compared to an algorithm using the original data may be achieved.

Figure 1:
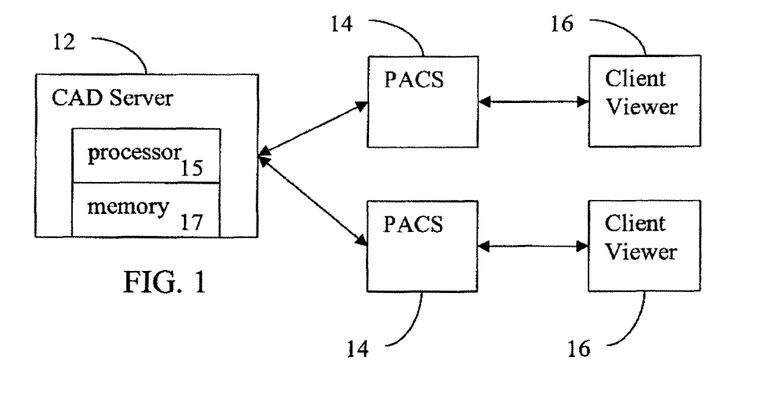
FIG. 1 is one embodiment of a network for computer assisted detection with medical scan data from a remote storage location.

FIG. 1 shows a system for computer assisted detection (CAD) with medical scan data from a remote storage location. The system includes a CAD server 12, one or more databases 14, and one or more client viewers 16. The CAD server 12 includes a processor 15 and a memory 17. In alternative embodiments, the system is only the CAD server 12 or the CAD server 12 is combined with or part of the database 14 in a same location or room. Additional, different, or fewer components may be used. For example, additional client viewers 16 are provided for interacting with one or more CAD servers 12 in a cloud computer environment. As another example, only one database 14 is provided.

The system allows any client viewer 16, such as client viewers associated with a hospital or medical organization or associated with a picture archiving service, to obtain CAD. The components of the system are remote from each other, such as the client viewer 16 being in a patient room, the database 14 being at a hospital for the patient or being part of a database in a separate facility, and the CAD server 12 being in the same or different facility as the database 14. The components are interconnected through one or more networks, such as the Internet or a local or wide area intranet. Secure data transmission is provided.

The CAD server 12 performs the CAD. The location results are provided to the database 14 and/or the client viewer 16. The client viewer 16 may receive the locations of landmarks associated with one or more detected features. The detection is performed on image data from the database 14. Since the CAD server 12 performs the CAD, the client viewer 16 may benefit from CAD without having to store, process, or update the CAD algorithm. The CAD server 12 may perform CAD for a plurality of different clients, including clients associated with the same or different medical institution. Any cloud-based client-server system or environment may be used.

The client viewers 16 are personal computers, tablets, laptop computers, personal digital assistants, cellular phones, workstations, or other devices for viewing detected locations and/or images. The client viewers 16 may be thin-clients, such as devices with insufficient memory or processing power for CAD in large medical image data sets. In one embodiment, the client viewers 16 are tablet or other handheld or mobile computers (e.g., personal data assistants or cellular phones). Medical professionals may carry with or have at their disposal the client viewers 16. Rather than requiring processing on and data transfer to the client viewers 16, the CAD server 12 detects locations and provides the locations to the client viewers 16. In alternative embodiments, the client viewers 16 have sufficient processing and/or memory for performing CAD, but rely on the CAD server 12 for data bandwidth or processing efficiency.

The client viewers 16 are the same type or different types of devices. For example, a nurse's station may have a workstation or personal computer operating as the client viewer 16, and another medical professional may have a tablet or cellular phone as the client viewer 16 while visiting a patient or making rounds.

The database 14 is a buffer, cache. RAM, removable media, hard drive, magnetic, optical, or other now known or later developed memory. The database 14 is a single device or group of two or more devices. In one embodiment, the database 14 is a picture archiving and communication system (PACS). The database 14 is configured by hardware and/or software to store, output, and/or compress medical scan data.

Separate databases 14 may be provided for redundancy, for efficient provision of the same data, for different institutions or groups, or for other reasons. Alternatively, one database 14 is provided. The database 14 is shown separate from the CAD server 12, but may be part of or located in a same facility or room as the CAD server 12.

The database 14 stores medical scan data. The medical scan data is data from computed tomography, ultrasound, positron emission, magnetic resonance, or other mode of scanning a patient. The medical scan data represents an interior area or volume of the patient. The scan data may be from a planar scan, a projection scan (e.g., x-ray), or from a tomographic scan (e.g., acquiring a plurality of slices or plane data to represent a volume). The medical scan data may be of different types or processes, such as being for a plurality of scans optimized to show different types of information (e.g., tissue and fluid types). In alternative embodiments, the CAD service may be provided for non-medical data, such as for geological surveys, structure analysis, image recognition, or other data intensive CAD operations.

The medical scan data is a three-dimensional data set or a sequence of such sets. The data represents a three-dimensional region. Any format may be used, such as voxels interpolated to a three-dimensional grid or data representing parallel or non-parallel planes. In alternative embodiments, the data represents a plane or other region.

The medical scan data is stored in any format. The format may be native to the scanning mode. Alternatively, the data is processed or the format otherwise changed. In one embodiment, the data is formatted pursuant to the digital imaging and communications in medicine (DICOM) standard. Any of the various image formats in the DICOM standard may be used.

The database 14 outputs the medical scan data in response to a request, a predetermined push, or other trigger. The medical scan data is output in the stored format or is processed for output. For example, the medical scan data is retrieved from storage and compressed. Any compression may be used, such as lossy compression. For example, the medical scan data is compressed pursuant to the JPEG 2000 standard. Lossless compression may alternatively be used. As an alternative, no compression is used. In other embodiments, the data is stored in a compressed format.

The CAD server 12 is a workstation, computer, server, processor, or other device for performing CAD. An interface to the network or database 14 and/or the client viewer 16 provides for communications, such as requests for CAD, requests for medical scan data, receipt of medical scan data, and output of locations or detected features. The interface is wired or wireless.

The CAD server 12 includes one or more processors 15 and memories 17. The CAD server 12 is configured by software and/or hardware to perform the CAD and communicate with the system. For example, instructions stored in the memory 17 configure the processor 15 to perform CAD and communicate the associated information. Additional, different, or fewer components may be provided for the CAD server 12.

The processor 15 is a general processor, digital signal processor, three-dimensional data processor, graphics processing unit, application specific integrated circuit, field programmable gate array, digital circuit, analog circuit, combinations thereof, or other now known or later developed device for processing medical scan data. The processor 15 is a single device, a plurality of devices, or a network. For more than one device, parallel or sequential division of processing may be used. Different devices making up the processor 15 may perform different functions, such as an automated anatomy detector and a separate device for communications associated with the detected anatomy.

The processor 15 receives the medical scan data from the database 14. The database 14 receives a request for particular scan data for a particular patient. The request is from the client viewer 16 and routed directly to the database 14 or routed through the processor 15. For example, a user selects a patient and an imaging session associated with the patient on the client viewer 16. In response, a request is sent to the processor 15. The processor 15 forwards a further request to the database 14 for the identified medical scan data. The memory 17 may include a list of data sets stored in each database 14. Alternatively, a request is sent to multiple databases 14 and the database 14 with the desired medical scan data responds. Any network communications process or format may be used to arrange for the medical scan data to be received from the database 14 by the processor 15. In another example, the request from the client viewer 16 is provided to the database 14, and the database 14 requests the CAD server 12 to perform CAD.

In one embodiment, the medical scan data is received by the CAD server 12 at progressively greater resolutions. Two or more resolution levels may be provided. For example, the database 14 outputs the medical scan data at selectable or predetermined resolution levels. Over time, data with greater resolution is received by the processor 15. The progressive resolution transmission may reduce the bandwidth requirements of the network at a given time.

Feedback from the processor 15 to the database 14 may provide further overall bandwidth reduction. The locations detected by the processor 15 at a given resolution are used to control the medical scan data to be requested and/or to control the medical scan data sent to the processor 15. Only data associated with detected locations in one resolution is received in the next greater resolution. The medical scan data received form the progressively greater resolutions is free of data representing regions outside of neighborhoods around detected candidate locations.

The medical scan data received at each progression for each neighborhood is only the higher resolution or higher frequency data. For example, a set of medical scan data representing a volume region is sent at a coarse or most coarse resolution. The database 14 generates the coarse set of data by an amount of compression. Alternatively, the database 14 down samples by any factor, such as a factor of ten or more, or other data reduction mechanism. For the next resolution level, data for one or more neighborhood regions detected from the coarse set is provided. The data is for voxels in the neighborhood but not provided with the coarse set. The additional data and the data for the coarse set for each neighborhood are combined by the processor 15 to form the higher resolution set of medical scan data. In one embodiment, the JPIP standard is used to transmit the higher resolution data as high frequency wavelet components for the specific neighborhoods.

By only sending the higher frequency information not provided for the neighborhood in a coarser set of data, further bandwidth reduction is provided. Alternatively, a complete set of data for a given resolution is received for each neighborhood.

In alternative or additional embodiments, the bandwidth for receiving the medical scan data is reduced by using compression. The database 14 stores data in a compressed format or retrieves the medical scan data and compresses the data for transmission. The compression is lossless or lossy.

The processor 15 receives the medical scan data and performs CAD. To perform the CAD, the medical scan data is decompressed, if received in a compressed format. Any decompression may be used. The compressed and/or decompressed data is stored in the memory 17 for CAD processing. The detection is performed on the decompressed medical scan data. Where lossy compression is used, the CAD may still operate despite data losses. Since the CAD algorithm is trained on data at different resolutions, detecting from data decompressed from lossy compression may provide sufficient detection. Alternatively, lossless compression is used to maintain all of the available data for a given resolutions.

The processor 15 detects one or more locations from the medical scan data. For example, the CAD algorithm detects possible tumors, blockages, restrictions, growths, organs, bones, or other structure. The detected location is a point, line, curve, area, surface, or volume.

The decompressed medical scan data is processed pursuant to any now known or later developed CAD algorithm to detect one or more candidate locations. In one embodiment, the processor 15 may perform machine learning and/or applies a machine-learnt algorithm. For example, the processor 15 applies a probabilistic model to detect a tumor or anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in medical scan data.

The processor 15 performs the detection hierarchally from the medical scan data at the progressively greater resolutions. In one embodiment, locations in an entire scanned volume or plane are detected from a coarsest set of data. Subsequent locations from higher resolution sets of data are detected from data representing neighborhoods associated with detected locations from a previous detection.

The classifier may include a plurality of models or classifiers (e.g., detectors) operable together or independently. For example, different probabilistic models are trained for different resolution levels. The probabilistic models may be joint or dependent. The locations detected in a coarser set are used to limit the data (e.g., the region) to which subsequent detection is applied.

The different classifiers for multiple resolution classification are the same or different types of classifiers. The same or different types of classifiers may be used for the same type of classification, such as different types of classifiers being used for different resolutions. In one embodiment, each probabilistic model is formed from a plurality of probabilistic boosting classifiers. Separate training and resulting machine-trained classifiers are provided for each resolution.

For application, the processor 15 calculates features for classification. The same or different features are used for classification in each resolution. Using a machine-trained translation classifier, each location in the data at the desired resolution is tested using the features associated with the location. If the classifier for a higher resolution does not detect a landmark in a given neighborhood around a location detected in a coarser resolution, then the neighborhood is ruled out. Only neighborhoods with subsequently detected locations are used for requesting higher resolution data and further detection.

The locations from the coarser resolution are used to identify the neighborhoods, but the specific voxels or detected locations are not otherwise used. Alternatively, the detected locations from the coarser data sets are propagated to higher resolution datasets. The features are used to rule out previous hypotheses (e.g., specifically detected previous locations), leaving a subset of remaining hypotheses.

The features are three-dimensional features. 3D data is used to calculate the features. The window function defining the data is a cube, but may have other volume shapes. The window is translated, rotated, and scaled as part of searching for a landmark. The same or different sized windows are used for different anatomies. In alternative embodiments, 2D data is used for calculating the features.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the "steerable" features described by Zheng, et al. in "Fast Automatic Heart Chamber Segmentation from 3D CT Data Using Marginal Space Learning and Steerable Features," Proc. Int'l Conf. on Computer Vision, pp. 1-8, 2007, are used. Other types of features may alternatively or additionally be used.

The memory 17 is a buffer, cache, RAM, removable media, hard drive, magnetic, optical, or other now known or later developed memory. The memory 17 is a single device or group of two or more devices. The memory 17 stores the medical scan data received by the CAD server 12 and/or data generated for the CAD. For example, data filtered for application of CAD is stored.

The memory 17 is additionally or alternatively a non-transitory computer readable storage medium with processing instructions. The memory 14 stores data representing instructions executable by the programmed processor 12 for data transmission in computer assisted detection. The instructions are for receiving transmitted data a progressive hierarchy of resolution and/or performing CAD on such data. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Progressive data transmission in combination with a respective hierarchy of classifiers are used to detect candidates for a given condition or structure. In other embodiments, the same approach is used to detect multiple or different types of landmarks. For detecting multiple types of landmarks, more data may be transmitted as a greater number of neighborhoods may be detected. Using progressive data transmission and hierarchal detection may still reduce the bandwidth.

The detected locations are stored in the database 14 with or separately from the medical image data. For example, a DICOM image with integrated or associated CAD markers is stored. Alternatively or additionally, the detected locations are output to a display, such as a display on the client viewer 16. The locations are displayed as coordinates or overlaid as markers on an image. An image of the region of the patient is displayed with detected anatomy or CAD marker graphics. The image may be at any resolution and may be for the entire volume region or sub-sets. For example, neighborhood regions are output with CAD markers. Alternatively or additionally, a value of a measurement associated with the detection is displayed. The value may be displayed in a chart, graph, and/or on an image.

Figure 2:
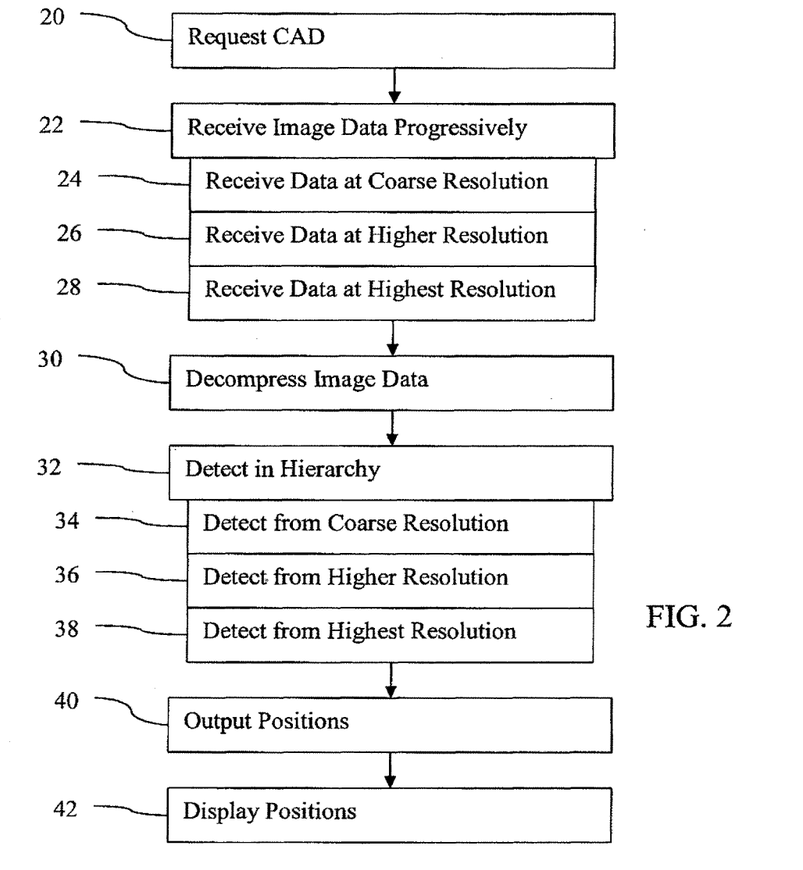
FIG. 2 is a flow chart diagram of one embodiment of a method for computer assisted detection with data from a remote storage location.

FIG. 2 shows a method for computer assisted detection with data from a remote storage location. The method is implemented by a medical diagnostic imaging system, a review station, a workstation, a computer, a PACS station, a server, combinations thereof, or other device for image processing scan data. For example, the system or computer readable media shown in FIG. 1 implements the method, but other systems may be used.

Figure 3:
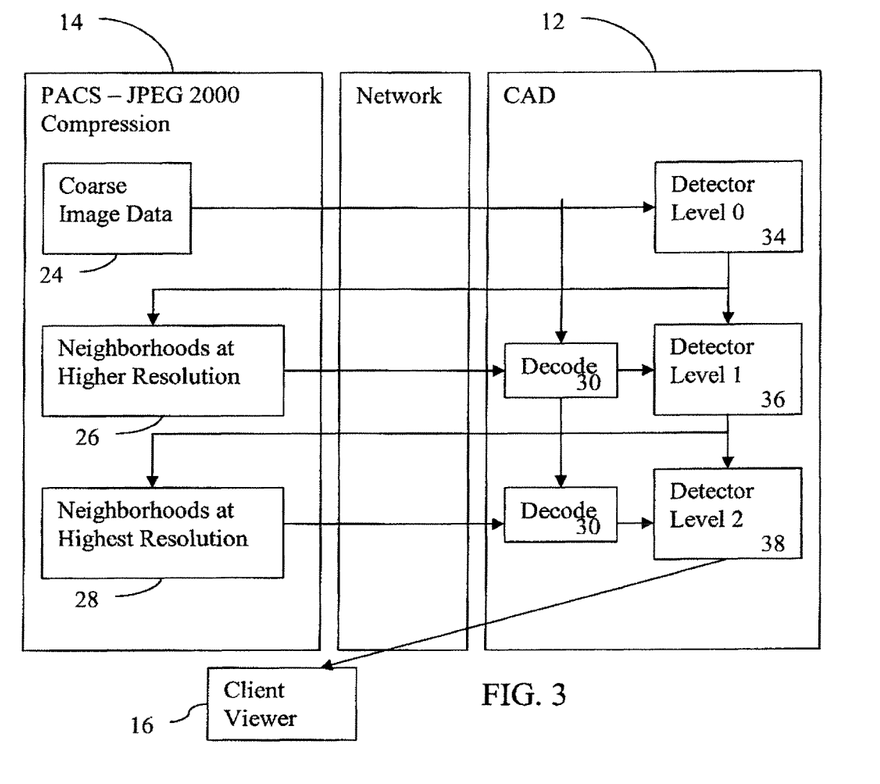
FIG. 3 is an example illustration of another embodiment of a method for computer assisted detection with data from a remote storage location implemented on an example network.

FIG. 3 shows one embodiment of the method of FIG. 2 as implemented on the system of FIG. 1. A single client viewer 16 is shown for describing the flow, but additional client viewers 16 may be provided for operation with a given CAD server 12 and/or database 14. The database is specifically represented as a PACS system operating with JPEG 2000 compression. Other compression and/or databases may be used. The CAD sever 12 is positioned between the client viewer 16 and database 14 to represent an alternative communication route than shown in FIG. 1. The client viewer 16 communicates with the CAD server 12, which requests data from the database 14.

The method is implemented in the order shown or a different order. Additional, different, or fewer acts may be performed. For example, acts 28 and 38 are not provided. As another example, receipt of data and detection are performed for one resolution but using lossy compression. In another example, acts 20, 30, 40 and/or 42 are not provided.

In act 20, CAD service is requested. A medical professional uses a client device 16 or other input to request CAD. Positions associated with a landmark, such as anatomy, lesions, tumors, or other structure, are desired. The client device requests CAD service by a remote processor. The CAD service acts as a second pair of eyes or outputs candidate locations for review by a medical professional.

The request is for application of algorithms for automatic detection of landmarks in 3D volumes or 2D planes in a cloud computing environment. The request is sent to a CAD processor or a database for storing the associated data. The detection algorithm requests data from a database, such as PACS server, or the request is routed to the database. In one embodiment, the request is for detection in a cloud (DiC). For example, a client requests the display of an anatomical part for a specific patient. The detection in the cloud detects the part and provides a model of the anatomy, a location of the anatomy, and/or an image with the anatomy highlighted.

In act 22, image data is received in response to a request for CAD service. The data is received from a network, but may be received from portable media in other embodiments. The image data is received at a computer assisted detection processor and from a remote storage location. For example, the computer assisted detection server receives the image data in a DICOM format from a picture archiving server. The patient data stored in a data center is transmitted to a high performance data analysis server that runs the detection algorithm.

The image data represents a patient. The image data is from any medical imaging modality capable of scanning a patient. The image data corresponds to data representing planes, data representing a volume, data representing a sequence of volumes, data in a polar coordinate format, data in a Cartesian coordinate format (e.g., data interpolated to a regular 3D grid), displayed images, filtered data, or other data. The image data is data already used to generate an image or data to be used to later generate an image.

The volume region of the patient includes tissue, fluid or other structures. The shape of a structure or spatial aspect may be reflected in the image data. In other embodiments, the data represents the earth, ocean, or other object.

Data from any mode of scanning may be used. For example, computed tomography (CT) data, magnetic resonance data, ultrasound data, positron emission data, fluoroscopy data, x-ray data, or other medical scan data is received. In one example embodiment, the image data is from a CT scan. The CT data represents a volume and is acquired as 80-350 slices with 153×153 to 512×512 pixels for each slice. The in-slice resolution is isotropic and varies between 0.28 to 1.00 mm with a slice thickness from 0.4 to 2.0 mm. Data for an ultrasound volume may have lesser or greater amounts of data. Data for a magnetic resonance scan may have greater or lesser amounts of data. The images stored on the database often are hundreds of megabytes in size, especially for data representing a 3D volume or sequences of such volumes.

Due to the memory or processing power of the client device 16, it may not be possible to process the image data on the client directly. The large sizes and limited bandwidth over the network (e.g., between client device 16. CAD server 12, and/or data center 14 (e.g. PACS server) may present a problem for cloud-based CAD. Depending on the bandwidth, the transmission of such large datasets may take tens of seconds or even minutes. This complicates the workflow in interactive applications. Results may not be available immediately or quickly. Results may be further slowed where several detection requests are made simultaneously, requiring bandwidths of tens of GBits/second.

In one embodiment, compression is used to reduce the bandwidth. For example, lossless compression is provided, such as associated with the 3D JPEG 2000 standard.

Greater bandwidth reduction is provided with lossy compression. The image data is received in a lossy compression format. For example, the image data is received pursuant to the JPEG 2000 Interactive Protocol (JPIP). Data transmission is performed pursuant to the JPIP format, but other compression formats may be used. The detection results may also be efficiently visualized by the client via JPIP protocol. Lossy compression may not hinder the final detection accuracy or may hinder the detection accuracy, but not unacceptably so.

Progressive data transmission may be used as an alternative or in addition to lossy compression. Due to the volume of data, the data is received at progressively greater resolutions to limit bandwidth requirements. Acts 24-28 show receipt of the image data at three different resolutions. Data is received at a coarsest resolution in act 24 and at a final or highest resolution in act 28. The data is received at an intermediate resolution in act 26. Additional or fewer resolution levels may be used.

The coarsest and finest resolution levels may be of any resolution. The acts 24-28 are shown for the relative resolution between the levels. The difference in resolution between levels may be a linear or non-linear change, such as changing by a power of two for each resolution level (e.g., decimated by a factor of 8 for the coarsest level, then a factor of 4, then a factor of 2, and finally not decimated in a four resolution level system). In one embodiment, the difference in resolution between any two levels is at least a factor of 1.25, such as down sampling, compressing, or filtering an original data set by 1.25 to form data at a more coarse resolution and using the original data and associated resolution for the finer resolution level in a two resolution example.

In the example of FIG. 3, the CAD server 12 receives the image data at different times and different resolutions in acts 24, 26, and 28. The progression of the data transmission and receipt is from most or more coarse resolution to finest or finer resolution. The CAD server 12 operates on the progressive data in an efficient hierarchical detection system to avoid the problem of transmitting large datasets. The CAD detection runs on the CAD server 12, which obtains portions of the original dataset from the PACS server 14 on demand, such as using the JPIP protocol.

In act 24, the CAD server 12 receives data. The data is at a relatively coarse resolution, such as representing a volume at 256×256×256 voxels. This relatively coarse resolution is down sampled or compressed from data representing the same volume at 1024×1024×1024 voxels. Other relative resolutions or absolute resolutions may be used. The data is received at the coarsest resolution in response to a request sent to the database 14 from the CAD server 12. The CAD server 12 requests the data in response to a trigger or request from the client viewer 16.

In act 26, the CAD server 12 receives additional data. The additional data is received in response to a further request from the CAD server 12. The additional data represents the volume at a finer resolution. For example, the additional data represents the same volume at 512×512×512 voxels. This resolution is finer than the resolution of the data provided in act 24, but coarser than the original volume.

To use less bandwidth for transmission at any given time, the additional data avoids repetition of any data provided earlier or already in any coarser sets. The values for voxels received in act 24 are not sent again. In the example above, half of the 512×512×512 set of voxel values are sent in act 24. Only the other half of the voxel values are sent. The bandwidth requirement at any given time is reduced as compared to sending the entire original set of voxels or even sending the reduced resolution 512×512×512 set of voxel values.

In one embodiment, the JPEG 2000 Interactive Protocol (JPIP) is used to transmit the data at different resolutions. JPIP provides for avoiding repetition in data pyramids. The resolution maps to the frequency of the wavelet components in compression. The coarsest set of data provides the lowest frequency wavelet components. The additional data representing the higher resolution includes higher frequency wavelet components. The higher frequency wavelet components not in the coarser sets of data are transmitted and received. The image data at the progressively greater resolutions includes high frequency wavelet components not in previously received image data at lesser resolutions. The image data at the progressively greater resolutions does not include wavelet components of previously transmitted and received data. The data at each resolution level is compressed.

Different or additional bandwidth reduction is provided by coordinating the progressive data transmission and receipt with the hierarchal detection of act 32 (acts 34-38). In addition to being non-repetitive, the additional data is for neighborhoods around the candidate locations detected from the previous data. Regions around the coarse candidate locations detected from the data received in act 24 are defined. The regions may be of any size. For example, a 16×16×16 region is provided around each candidate location detected from the preceding data set. As another example, larger neighborhoods are sued, such as 100 mm at a coarse resolution and 40 mm at a fine resolution. The neighborhoods are sized to allow sufficient data to compute features for detection. The neighborhood may be sized and shaped based on groupings of candidate locations or other considerations. For example, the neighborhood is larger for regions with multiple candidate locations within a given distance from each other.

The candidate locations define the locations and sizes of finer resolution sub-images or data that are used to refine the candidate locations at the next detection level. The detected locations at one resolution level are used to bootstrap the data used for detection in the next level. The neighborhoods, based on the candidate locations, define the additional data to be transmitted and received for detection at the next resolution level. Non-repetitive data only around the candidate locations is requested and/or received. Data representing other portions of the volume or regions outside of the neighborhoods is not requested and/or received. The JPIP standard provides for region-based provision of data at different resolutions (e.g., different amounts of compression).

Figure 4:
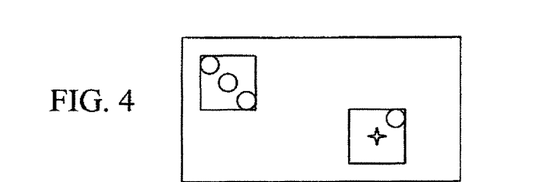
FIG. 4 is a graphical example of detected locations in a first resolution level.

FIG. 4 shows an example where the coarsest data set represents the large rectangular box. The data represents two dimensions, but may represent three dimensions. The small circles represent candidate locations detected from the coarsest data. The star represents both a candidate location detected from the coarsest data and a ground truth or actual landmark being sought. The squares are neighborhoods defining the data to be provided at a higher resolution. The data outside the squares is not provided. The additional data corresponds to detected candidate locations, so the received data is free of data representing regions outside of neighborhoods around the candidate locations. This bandwidth reduction is provided for any of the progressively greater resolutions.

In act 28, the computer assisted detection processor (e.g., CAD server 12) requests and receives additional data. The additional data represents neighborhoods around the candidate locations detected using the data received in act 26. To reduce bandwidth, the additional data is compressed. To further reduce bandwidth, data from regions outside the neighborhoods defined by locations detected in act 36 is not received.

While shown as three levels of progressive data receipt, additional levels may be provided. The refinement continues until all levels of the hierarchy have been processed. Where a candidate location is not detected for a given neighborhood, higher resolution data for that neighborhood is not requested or received.

Since the data does not reside on the CAD server 12, the hierarchical detection algorithm allows for bandwidth savings. First, the algorithm processes candidate regions at finer resolution rather than the entire images. A feedback loop is incorporated where the candidates from the coarse levels are refined in the finer levels. The coarsest image is transmitted in its entirety, but finer resolution data is sent just for portions of the entire image (e.g., original volume set). Only small regions surrounding the most reliable candidates are used in the refinement at subsequent levels. Second, the transmitted images or sub-images are compressed with a lossy or lossless compression, such as JPEG 2000 compression, resulting in a coarse resolution image and a hierarchy of wavelet coefficients. Only high frequency wavelet components are transmitted at the higher resolution levels. When combined, these components may result in a more than 50 times overall reduction of the original image size on average.

In act 30, the received data is decompressed. Where compression is used, the reverse transform is applied. The CAD server 12 decodes the received data, such as converting from the wavelet components to image data or voxel values.

Data representing the same region, but at different resolutions, may be combined. For example, data representing neighborhoods at a finer resolution is combined with the data representing the neighborhoods at the coarser resolution. The combined data forms the data at the finer resolution. For each receipt of data at a finer resolution, the data is combined to form the finer resolution data for the neighborhood.

In act 32, candidate locations are detected. A processor performs CAD on the data. The processor detects from uncompressed data derived from the compressed data. Any now known or later developed CAD process may be used.

In one embodiment, a hierarchy of detection is performed. Classifiers designed or trained for detection at different resolutions for one or more types of candidates are applied to the data at the different resolutions. For example, a hierarchy of machine-trained detectors detects candidate locations. Detection is performed hierarchally on the image data at the progressively greater resolutions.

Candidate locations from each detection are feed back to identify the neighborhoods for which subsequent detection is to be performed. The specific candidate locations are not otherwise used in the subsequent detection, but may be in other embodiments. The image data for each of the resolutions represents regions around the candidate locations detected from a lesser one of the resolutions.

In the hierarchical learning algorithm, one detector is trained for each level. At each level, the search region is defined by the neighborhoods surrounding the highest probability candidates from the previous level. As the detection continues over the levels, the image regions are progressively obtained over the network from the PACS server 14 for further detection.

A coarse-to-fine pyramid of classifiers are trained and applied. The position candidate hypotheses are propagated from the coarser levels to the finer levels. At the coarsest resolution, $r_0$, a detector $D(r_0; q)$ for detecting the parameters $\theta_0$ of the target landmark is trained using the volume region V $(r_0; q; R_0)$. The size $R_0$ of the region is the size of the whole image at resolution $r_0$. q is a quality factor. The quality q may be measured by a peak signal-to-noise ratio, pSNR. The quality q is lower for images with artifacts caused by image compression. The pSNR value is determined with respect to the uncompressed image, which has the highest quality ~q. In alternative embodiments, quality is not used as a variable for the detector other than selecting the detector with the best sensitivity or other performance consideration.

The detector is then used to obtain position candidate hypotheses at this level. The candidates with the highest probability are bootstrapped to train a detector $D(r_1; q)$ at the next level with resolution $r_1$. The volume region V $(r_1; q; R_1)$ is composed of the union of neighborhood regions of size $R_1$ surrounding the position candidates. The bootstrapping procedure continues until all resolution levels r have been processed. The bootstrapping makes it possible to use more candidates initially and to train another more focused classifier at a finer level.

The hierarchical processing tests a larger context in the coarser level. For each greater resolution, the search space is tighter. This may help to avoid local maxima of the probability distribution that would otherwise cause false positives. The search step may depend on the resolution at each level and does not need to be chosen to balance the accuracy of the final result and computational speed. The multi-level hierarchy may increase efficiency through the recursive decrease of the search subspace size R. The decrease in the subspace size makes it possible to reduce the size of the data requested by the algorithm.

Figure 5:
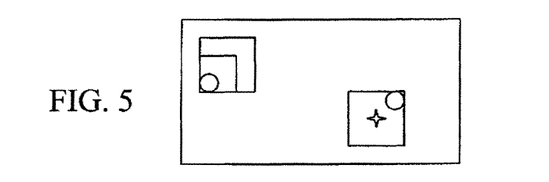
FIG. 5 is a graphical example of detected locations in a second resolution level.

FIGS. 4 and 5 show hierarchal detection at two resolution levels with bootstrapping of the candidate locations at each resolution. FIG. 4 represents detection of five candidate locations with sufficient probability. Some of the detected candidate locations are near the actual landmark (star) and others are grouped in another location. The grouping away from the actual landmark may result in a false positive. Higher resolution data is requested and received for the neighborhoods (squares) around the groups of candidate locations.

FIG. 5 represents detection from the higher resolution data. The detector for the next resolution is applied to the higher resolution data representing the neighborhoods (squares from FIG. 4) and not the entire plane (rectangle). The detection is performed for the neighborhood without identifying the specific locations previously detected. Most of the false positive candidates are eliminated. In an alternative embodiment, only the candidate locations from the previous detection are tested. The higher resolution data is used for calculating features associated with the candidate locations.

The small square around the false positive spaced from the ground truth defines another neighborhood for the next highest resolution. For any neighborhoods where no candidate locations are of sufficient probability, no further data is requested and the region is ruled out as having the landmark. The detection will be refined within a search space for each candidate at the next level.

The classifier used for each resolution is the same or different. The features used by the classifier or to train the classifier are the same or different for each classifier. In one embodiment, a robust learning-based algorithm includes a stage for each resolution. The same or different algorithms are used for different types of data (e.g., ultrasound, CT, MRI) and/or type of landmark to be detected (e.g., anatomy, tumor, or restriction).

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifiers are trained from a training data set using a computer. Any number of expert annotated sets of data is used. For example, about 200 volumes representing an anatomy of interest are annotated. The annotation indicates one or more landmarks within the volumes. The different landmarks of each volume are annotated. A database of known cases is collected for machine learning, providing a database-driven knowledge-based approach. For training data, three-dimensional context information is preserved and guides the detection process. The detectors are trained on a large number of annotated 3D volumes. This large number of annotations allows use of a probabilistic boosting tree to learn relevant features over a large pool of 3-D Haar, steerable, and/or other features. Haar and steerable features may be efficiently computed and be effective as a feature space for boosting classifiers. Other features may be used. Each classifier uses the data sets and annotations specific to the landmark being classified.

In one embodiment, the classifier is a knowledge-based probabilistic model, such as a marginal space learner. The classifier learns various feature vectors for distinguishing between a desired landmark and information not being detected. In alternative embodiments, the classifier is manually programmed. For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the landmarks are extracted and learned in a machine algorithm based on the experts' annotations, resulting in a probabilistic model. A large pool of features may be extracted. The training determines the most determinative features for a given classification and discards non-determinative features. Different combinations of features may be used for detecting different landmarks and/or the same landmarks at different resolutions. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

The probabilistic boosting tree (PBT) unifies classification, recognition, and clustering into one treatment. A probabilistic boosting tree is learned for each resolution. The classifier is a tree-based structure with which the posterior probabilities of the presence of the landmark of interest are calculated from given data. Each detector not only provides a binary decision for a given sample, but also a confidence value associated with the decision. The nodes in the tree are constructed by a combination of simple classifiers using boosting techniques, such as disclosed by Tu, "Probabilistic Boosting-Tree: Learning Discriminative Models for Classification, Recognition, and Clustering," Proc. Int'l Conf. on Computer Vision, pp 1589-1596, 2005.

The machine-learnt classifiers are trained using the training data. The learnt classifiers may be applied to test data. The test data has a known ground truth, such as through manual designation. The learnt classifiers may be applied to data for a patient. The data for the patient does not have an annotated ground truth.

In one embodiment, discriminative learning is used to determine the candidate locations. For example, anatomical landmarks are detected by a learning-based technique for efficient 3D object detection. Each landmark is represented by its position $\theta=(px; py; pz)$. The goal of the system is to automatically estimate the set of position parameters $\theta'$ using a volumetric context surrounding the landmark position: $\theta'=\arg\max_\theta P(\theta|V)$, where $P(\theta|V)$ is the probability of the parameters given the image volume. A random variable y in the range of −1 to +1 is assigned, where y=+1 indicates the presence and y=−1 indicates the absence of the anatomy. A Probabilistic Boosting Tree classifier (PBT) is trained such that posterior probabilities can be computed. Each node of the PBT is an AdaBoost classifier that is trained to select those features that best discriminate between positive and negative examples of the landmark. The probability of a landmark being detected is provided as $P(y=+1|\theta;V)$. The equation for the position parameters may be rewritten as: $\theta'=\arg\max_\theta P(+1|\theta;V)$. The robustness of the discriminative AdaBoost framework makes it possible to use noisy images in training and testing and still obtain final detection results with high accuracy.

Lossy compression may result in artifacts. For example, lossy 3D JPEG 2000 compression may cause artifacts. The classifier is adapted to different levels of compression (i.e., different levels of resolution) of the input data. The hierarchal detector trained using data progression even with lossy compression may be better then training on uncompressed data. The hierarchal classifier may learn the consistent anatomical structures and ignore the compression artifacts.

In act 34, candidate locations are detected from image data at a most coarse resolution. The detection is performed on data that was compressed and transmitted to the CAD server 12. The coarsest resolution is relative to other resolutions used for detection and is not necessarily the coarsest resolution that may be achieved from an original data set. The CAD algorithm starts detection on a down sampled low resolution data set representing an entire volume. Alternatively, the data represents only a portion of an entire scanned volume.

The classifier detects one or more candidate locations. None, one or more of the set of candidate locations may be the actual landmark sought by the classifier. The number of candidate locations may be predetermined. For example, the machine-trained or other detector determines a probability for each voxel in the data being the landmark. The voxels associated with the highest 20-100 probabilities are selected as the candidate locations. In other embodiments, the probability value is used. For example, the locations associated with a probability over a threshold are selected. Other approaches or combinations of these approaches may be used to select a collection of candidate locations.

The detected candidate locations are used to select data to be received or transmitted. Finer resolution data is requested for neighborhoods around each of the candidate locations. The finer resolution data is received or data for forming the finer resolution is received, such as receiving higher frequency wavelet components to be used with previously received lower frequency components to form the finer resolution data.

In act 36, the machine-trained detector for the next resolution level is applied. The decoded and combined data for the neighborhoods associated with candidate locations detected in act 34 are used to calculate the features for act 36. The same or different features are used for the different resolutions.

Candidate locations are detected from the finer resolution data. The computer-assisted detection applies the classifier for the given resolution to the data representing the union of the neighborhoods. More, fewer, and/or different candidate locations are detected. For a given neighborhood, no candidate locations may be detected. As a result, the neighborhood and corresponding previous candidate locations are ruled out.

The same or different selection criteria are applied to the selection of candidate locations. For example, a predetermined number of locations are selected, so only locations associated with the highest probabilities are selected. As another example, a threshold of sufficient probability is applied. The threshold or number is the same or different than applied in act 34.

Since another detection is provided in the hierarchy of the example embodiments of FIGS. 2 and 3, the candidate locations are used to define neighborhoods for requesting even higher resolution data. Only candidates with the highest probability are retained, and their surrounding neighborhoods are used to obtain image regions at the next level of detection.

In act 38, detection based on the next resolution level is performed. A separate detector trained at the appropriate resolution level is applied.

The selection of candidate locations uses the same or different criteria than selection in acts 34 and 36. Since act 38 outputs the final candidate locations, a more stringent criterion may be used to reduce the number of candidate locations. Sensitivity analysis may indicate more or less inclusive criteria to decrease false positives and avoid ruling out actual positives.

In act 40, the candidate locations are output. The positions within the volume of the detected landmarks are output. The locations detected at the greatest resolution are functions of the locations from the other resolutions. The final detection results are obtained by robustly aggregating strongest candidates from the finest level. The locations from the highest resolution are output as the possible detected landmarks.

The locations are output to the client device 16. For example, positions are output to a handheld client device 16 that requested the CAD service. The client device 16 separately receives an image, such as a rendering from the volume data or a planar reconstruction from the volume data. The image is highlighted by the client device 16 with the highlighted landmarks in the relevant locations. Alternatively or additionally, the locations are output to the database 14. The database 14 stores the locations with the data, such as the medical scan data representing the volume. For example, the results are stored with the original study on the PACS server.

In an alternative embodiment, the CAD server 12 generates an image with the landmarks highlighted. The image is output rather than or in addition to the locations. The image represents the locations, but the locations may not be specifically output (i.e., x, y, z coordinates not output).

In act 42, an image with the positions is displayed. The candidate locations are highlighted with markers, such as stars, boxes, outlines, or other shapes. Color may alternatively or additionally be used to mark the candidate locations in the image. The image is of the patient and is generated from the data used to perform the detection. Alternatively, spatially registered data other than used for detection may be used to generate the image.

In one embodiment, the image is a volume rendering from the volume data used for detection. One rendering or multiple renderings from the same volume may be displayed. The detected landmarks are displayed in the image.

The effects of the compression artifacts on training and detection may be evaluated. Compressed images may have worse quality, such as measured by pSNR, than original images. However, training on previously compressed images may result in lower average detection errors. The hierarchical learning algorithm may be robust, reduce computation time, reduce bandwidth requirements, and have lower detection error than a classifier trained only on the finest resolution image. Other comparisons may be made, such as a system trained on a multi-resolution hierarchy of uncompressed images being compared with a hierarchy trained with lossy compression.

In an example embodiment, a full body CT data set is used. 86 CT volumes are used for testing in one example using a system trained on 161 volumes. The original images are resampled to 4 mm isotropic resolution. The average size of the volumes is 97×80×165 voxels. The landmark of interest is the right hip bone landmark.

The training and testing datasets are disjoint and the volumes in each are chosen randomly. The images are compressed at different pSNR levels. The classifiers are trained with images at each compression level and also with the original uncompressed images. The detection error statistics are then computed for images with different pSNR levels with models trained on (a) images with the same level of pSNR and (b) uncompressed images. Better performance may be obtained when training on compressed images. Even though the training images have worse quality, the strength of the boosting classifier is the ability to adapt to the training data and ignore inconsistencies caused by the image artifacts. This is accomplished through the feature selection at each training step. The median of the 80% smallest errors may be plotted against the average volume size computed for each pSNR level. By training on compressed images, smaller detection errors for a given compression level may result than when training only on uncompressed images. For example, the final detection error is 6 mm with average compressed volume size of 25 kB at 16 mm resolution. The average uncompressed volume size is 51 kB.

In a first case to evaluate the robustness of the hierarchical processing, images with 8 mm resolution are used in training and testing. In a second case, 16 mm and 8 mm images are used for training a hierarchical classifier with bootstrapping of the locations. The hierarchical approach may result in lower detection errors for a given average volume size. This may be especially apparent for heavily compressed images. The hierarchal approach may be more efficient. Smaller data sizes are used in detection, resulting in reduced bandwidth requirement for remotely accessing the data.

The overall system with 16-8-4 mm hierarchy using uncompressed images may be compared to using images compressed at pSNR 70. The hierarchical system is also compared to a simple algorithm operating on uncompressed images with a single resolution of 4 mm. An algorithm trained on images compressed with lossy compression may achieve data size reduction by a factor of 3.7 when compared to a hierarchical training on lossless-compressed images, by a factor of 12.7 when compared to an algorithm operating on a single resolution of 4 mm, and by a factor of 30.0 when the original (uncompressed) images are used. The average detection error is comparable for all three cases.

In another embodiment, a brain MRI data set is used. 384 MRI volumes are used for training, and 127 volumes are used for testing. The original images are resampled to 2 mm isotropic resolution. The average volume size is 130×130×101 voxels. In each volume, the crista galli (CG) landmark of the brain is detected.

Using the brain MRI data, the robustness of the hierarchical processing may be better. For example, images with 2 mm resolution are used in training and testing. In the second case, 4 mm and 2 mm images are used to train a hierarchical classifier with bootstrapping. The hierarchical detection algorithm may result in lower detection errors for a given average volume size. The robustness of the hierarchical approach and the bandwidth reduction may be provided.

For detection in a cloud, a system for anatomical or other landmark detection is provided in a cloud computing environment. A hierarchical learning algorithm propagates position candidate hypotheses across a multiresolution hierarchy during training and detection. The total bandwidth savings for retrieving remotely stored data may amount to 50 times (CT data) and 300 times (MRI data) reduction when compared to the original data size.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for data transmission in computer assisted detection, the storage medium comprising instructions for:

receiving, at a computer assisted detection processor and from the remote storage location, first data, the first data comprising down sampled data of data representing a region;

detecting, by the computer assisted detection processor, a plurality of first locations of a spatial aspect of structure represented by the first data;

requesting and receiving, at the computer assisted detection processor, second data, the second data comprising additional data representing second neighborhoods around the first locations and not representing portions of the region outside of the second neighborhoods;

detecting, by the computer assisted detection processor, a plurality of second locations of the spatial aspect of the structure represented by the second data; and outputting positions to a client device different than the computer assisted detection processor and the remote storage location, the positions being a function of the second locations.

2. The non-transitory computer readable storage medium of claim 1 wherein receiving the first data comprises receiving the first data in a lossy compression format, and further comprising:

decompressing the first data;

wherein detecting the first locations comprises detecting from the decompressed first data.

3. The non-transitory computer readable storage medium of claim 1 wherein the second locations include one or more of the first locations, the detecting of the second locations ruling out at least one of the first locations.

4. The non-transitory computer readable storage medium of claim 1 wherein the first data and second data are compressed data pursuant to the JPEG 2000 Interactive Protocol.

5. The non-transitory computer readable storage medium of claim 1 wherein the first data comprises compressed data at a first level and the second data comprises compressed data at a second level less than the first level.

6. The non-transitory computer readable storage medium of claim 1 wherein the second data comprises high frequency wavelet components not in the first data.

7. The non-transitory computer readable storage medium of claim 1 further comprising:

requesting and receiving, at the computer assisted detection processor, third data, the third data comprising additional data representing third neighborhoods around the second locations and not representing portions of the region outside of the third neighborhoods; and detecting, by the computer assisted detection processor, a plurality of third locations represented by the third data;

wherein outputting comprises outputting the positions as the third locations.

8. The non-transitory computer readable storage medium of claim 1 wherein outputting comprises outputting the positions to the client device, the client device comprising a handheld device;

further comprising:

requesting, by the client device, the positions for a patient, wherein the remote storage location comprises a picture archiving server; and displaying the positions on an image rendered remotely from the client device, the image being of the patient and rendered from the data representing the region.

9. In a non-transitory computer readable storage medium having stored therein data representing instructions executable by a programmed processor for data transmission in computer assisted detection, the storage medium comprising instructions for:

receiving, at a computer assisted detection processor and from the remote storage location, first data, the first data comprising down sampled data of data representing a region;

detecting, by the computer assisted detection processor, a plurality of first locations represented by the first data;

requesting and receiving, at the computer assisted detection processor, second data, the second data comprising additional data representing second neighborhoods around the first locations and not representing portions of the region outside of the second neighborhoods;

detecting, by the computer assisted detection processor, a plurality of second locations represented by the second data; and outputting positions to a client device different than the computer assisted detection processor and the remote storage location, the positions being a function of the second locations;

wherein detecting the first locations comprises detecting with a first machine-trained detector and wherein detecting the second locations comprises detecting with a second machine-trained detector, wherein the first locations are a collection of locations associated with a threshold probability output by the first machine-trained detector;

further comprising:

bootstrapping the first locations to the second machine-trained detector, the second machine-trained classifier detecting from a union of the second neighborhoods.

10. The non-transitory computer readable storage medium of claim 1 wherein detecting the second locations comprises detecting from a combination of the first and second data for the second neighborhoods.

11. A method for computer assisted detection with data from a remote storage location, the method comprising:

receiving image data representing a patient at progressively greater resolutions; and detecting, by a processor, candidate locations of structure in the patient hierarchally from the image data at the progressively greater resolutions where the image data for each of the resolutions is for the candidate locations of the structure in the patient detected from a lesser one of the resolutions;

wherein the received image data is free of data representing regions outside of neighborhoods around the candidate locations for any of the progressively greater resolutions.

12. The method of claim 11 wherein receiving comprises receiving first image data at a first resolution level, wherein detecting the candidate locations comprises detecting first candidate locations from the image data at the first resolution level;

further comprising:

feeding back the first candidate locations;

wherein receiving comprises receiving second image data corresponding to the first candidate locations, and wherein detecting the candidate locations comprises detecting second candidate locations from the second image data.

13. The method of claim 11 wherein receiving comprises receiving the image data at the progressively greater resolutions as lossy compressed data, and wherein detecting comprises detecting from uncompressed data derived from the lossy compressed data.

14. The method of claim 11 wherein the progressively greater resolutions comprise at least first and second resolution levels, the first resolution level being more coarse than the second resolution level, and wherein detecting hierarchally comprises detecting from the image data at the first resolution level, using the candidate locations from the detecting the at first resolution level to select the image data at the second resolution level, and detecting the candidate locations at the second resolution level from the selected image data.

15. The method of claim 11 wherein receiving comprises receiving the image data pursuant to the JPEG 2000 Interactive Protocol, the image data at the progressively greater resolutions comprising high frequency wavelet components not in previously received image data at lesser resolutions.

16. The method of claim 11 further comprising:
outputting, to a client handheld device, the candidate locations detected from a greatest resolution of the progressively greater resolutions; and
wherein receiving comprises receiving by a computer assisted detection server from a picture archiving server, the computer assisted detection server comprising the processor.

17. The method of claim 11 wherein detecting comprises detecting with hierarchy of machine-trained detectors.

18. A system for computer assisted detection with medical scan data from a remote storage location, the system comprising:
a database configured to store the medical scan data and configured to output the medical scan data in a lossy compression format, the medical scan data representing a region of a patient; and
a processor configured to receive, through a network, the medical scan data from the database in the lossy compression format, the processor configured to decompress the medical scan data and detect a location of structure of the patient in the region from the decompressed medical scan data.

19. The system of claim 18 wherein the processor is configured to perform the receiving the medical scan data at progressively greater resolutions and is configured to perform the detection hierarchally from the medical scan data at the progressively greater resolutions;
wherein the medical scan data received form the progressively greater resolutions is free of data representing regions outside of neighborhoods around detected candidate locations, the location being one of the detected candidate locations.

20. The system of claim 18 wherein the lossy compression format comprises a JPEG 2000 format.

* * * * *